United States Patent [19]

Evans et al.

[11] Patent Number: 5,312,425
[45] Date of Patent: May 17, 1994

[54] ATHERECTOMY DEVICE HAVING HELICAL BLADE AND BLADE GUIDE

[75] Inventors: Michael Evans, Palo Alto; Richard L. Mueller, Mountain View, both of Calif.

[73] Assignee: Devices for Vascular Intervention, Inc., Redwood City, Calif.

[21] Appl. No.: 44,131

[22] Filed: Apr. 7, 1993

Related U.S. Application Data

[60] Division of Ser. No. 971,697, Nov. 4, 1992, Pat. No. 5,226,909, which is a continuation of Ser. No. 726,626, Jun. 28, 1991, abandoned, which is a continuation of Ser. No. 405,906, Sep. 12, 1989, abandoned.

[51] Int. Cl.$^5$ ............................................. A61B 17/32
[52] U.S. Cl. ................................... 606/155; 606/170; 606/180; 604/22
[58] Field of Search .................. 604/22; 128/750–755; 606/159, 170, 171, 180

[56] References Cited

U.S. PATENT DOCUMENTS

| | | | |
|---|---|---|---|
| 3,320,957 | 5/1967 | Sokolik | 606/170 |
| 4,445,509 | 5/1984 | Auth . | |
| 4,653,496 | 3/1987 | Bundy et al. . | |
| 4,669,469 | 6/1987 | Gifford, III et al. | 606/159 |
| 4,696,667 | 9/1987 | Masch . | |
| 4,745,919 | 5/1988 | Bundy et al. . | |
| 4,772,258 | 9/1988 | Marangoni et al. . | |
| 4,781,186 | 11/1988 | Simpson et al. . | |
| 4,844,064 | 7/1989 | Thimsen et al. . | |
| 4,867,157 | 9/1989 | McGurk-Burleson et al. . | |
| 4,909,781 | 3/1990 | Husted . | |
| 4,926,858 | 5/1990 | Gifford, III et al. . | |

FOREIGN PATENT DOCUMENTS 0163502  12/1985  European Pat. Off. .

Primary Examiner—Stephen C. Pellegrino
Assistant Examiner—William W. Lewis
Attorney, Agent, or Firm—Townsend and Townsend Khourie and Crew

[57] ABSTRACT

An atherectomy catheter includes a catheter body having a cylindrical housing at its distal end. The cylindrical housing includes an elongate cutting aperture on one side thereof and a mechanism for severing atheroma which enters within the opening. In a first embodiment, the cutting mechanism comprises a circular cutting blade which is advanced over an elongate guide member which defines a path for the blade. Use of the guide means helps assure that the cutting blade will not be lost from the housing during use. In a second embodiment, a rotatable helical cutting blade is mounted within the housing. In that particular embodiment, the helical cutting blade can serve as the guide member for the circular cutting blade.

15 Claims, 4 Drawing Sheets

ATHERECTOMY DEVICE HAVING HELICAL BLADE AND BLADE GUIDE

This application is a division of application Ser. No. 07/971,697, filed Nov. 4, 1992, now U.S. Pat. No. 5,226,909, which was an FWC of application Ser. No. 07/726,626, filed Jun. 28, 1991, now abandoned, which was an FWC of application Ser. No. 07/405,906, filed Sept. 12, 1989, now abandoned.

BACKGROUND OF THE INVENTION

1. Field of the Invention

The present invention relates generally to the construction and use of vascular catheters. More particularly, the invention relates to atherectomy catheters having means for severing atheroma at their distal ends.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and coronary blood vessels which feed the heart. When deposits accumulate in localized regions of a blood vessel, blood flow is restricted and the person's health is at serious risk.

Numerous approaches for reducing and removing such vascular deposits have been proposed, including balloon angioplasty where a balloon-tipped catheter is used to dilate a region of atheroma, atherectomy where a blade or other cutting element is used to sever and remove the atheroma, and laser angioplasty where laser energy is used to ablate at least a portion of the atheroma. Of particular interest to the present invention are atherectomy devices and methods where a cutting blade is advanced past an opening in a housing at the distal end of a vascular catheter. By positioning the housing so that at least a portion of the atheroma passes through the opening, the atheroma can be severed by advancing the cutting blade. Typically, such cutting blades are circular and are rotated and advanced simultaneously to effect the desired cutting.

U.S. Pat. No. 4,669,469, and European patent application EPA 163 502, each illustrate exemplary atherectomy devices of the type just described, where the cutter housing is typically a rigid metal cylinder Rigid cutter housings, however, are problematic when the catheters are being used in small, tortuous blood vessels where the catheter tip must pass through curves having small radii. Moreover, difficulties have been encountered in containing the circular cutting blade within the housing. It has generally been necessary to limit the area of the opening in the housing in order to assure containment and smooth travel of the blade. Such an approach is disadvantageous, however, since it limits exposure of the blade to the atheroma and the amount of atheroma which may be severed in a single pass of the blade. While designs which provide for travel of the blade over a movable guide wire ameliorate the problem somewhat, they still require limitations on the window opening and do not provide the smoothness of travel which is desired.

To overcome the limitations inherent in the rigid housing design, the use of flexible cutter housings has been proposed. See, U.S. Pat. No. 4,781,186, describing the construction of atherectomy catheters having flexible cutter housings which may comprise a slotted metal or metal braid configuration. While the use of flexible housings provides an improvement in the ability to position the distal end of the catheter within tortuous portions of the vascular system, such flexible housings exacerbate the problems with guiding the cutting blade within the housing. In particular, the window openings in flexible cutter housings will tend to deform as the housing is flexed. To the extent the opening is widened, the risk of losing the cutter blade is substantially increased. The use of a guide wire is of no substantial benefit since it is unlikely that the curvature of the guide wire would match that in the housing. Thus, the guide wire will be unable to guide the cutting blade along the desired arc.

For these reasons, it would be desirable to provide methods and devices to facilitate the guiding of cutting blades within the distal housings of atherectomy catheters. In particular, it would be desirable to provide guide mechanisms which allow a circular cutting blade to follow the arc of a flexible housing while it is undergoing flexing stress while in use. Alternatively, it would be desirable to provide other cutting mechanisms within the distal housing which provide for severing the atheroma and which are inherently contained within the housing and which conform to bending of the flexible housings during use.

2. Description of the Background Art

U.S. Pat. Nos. 4,669,469 and 4,781,186, and European patent application EPA 163 502, the disclosures of which are incorporated herein by reference, are described above. U.S. Pat. No. 4,772,258, describes an angioplasty catheter having distal drilling head which circumscribes and is attached to a helical drive shaft. U.S. Pat. Nos. 4,653,496, and 4,745,919, each of which are incorporated herein by reference, describe helical cutting blades having sharpened tips which may be introduced into blood vessels to remove stenotic lesions.

SUMMARY OF THE INVENTION

According to the present invention, atherectomy catheters comprise a catheter body having a lumen extending between proximal and distal ends thereof. A cylindrical housing is secured to the distal end of the catheter body, and the housing includes a cutting aperture or window formed on one side thereof. A cutting mechanism is provided within the housing for severing atheroma which extends inward through the aperture when the catheter is positioned within a blood vessel and urged against region of stenosis. The cutting mechanism is particularly adapted to provide for effective cutting of the atheroma while minimizing the risk that the cutting mechanism might escape from the housing. In particular, the cutting mechanism is capable of conforming to the bending of a flexible housing, even when such bending results in deformation of the cutting aperture.

In a first embodiment of the present invention, the cutting mechanism comprises a circular cutting blade disposed within the housing and attached to a mechanism for advancing (and usually rotating) the blade past the cutting aperture. The cutting mechanism further comprises an elongate guide frame which is disposed axially within the housing adjacent the cutting aperture. The guide frame defines the desired cutting path of the circular cutting blade and comprises an open framework which allows the penetration of atheroma into its interior. In this way, the severed atheroma is collected within the guide frame. In a preferred embodiment, the guide frame is a helical coil, and a mechanism may be provided for rotating the coil to translate the severed atheroma therein to one end of the cylindrical housing. Alternatively, a tamping mechanism may be provided for urging the severed atheroma to one end of the housing. In some cases, it will also be desirable to provide sharpened edges on the helical coil so that rotation of coil will enhance severing of the atheroma.

In a second embodiment, a helical cutting blade is disposed within the cylindrical housing. A mechanism is provided for rotating the helical cutting blade, which causes a severing action for atheroma which is urged between adjacent turns of the helical blade. In this way, cutting is achieved without providing an additional cutting blade. A tamping mechanism may also be provided for urging the severed atheroma to one end of the cylindrical housing.

DESCRIPTION OF THE SPECIFIC EMBODIMENTS

Figure 1:
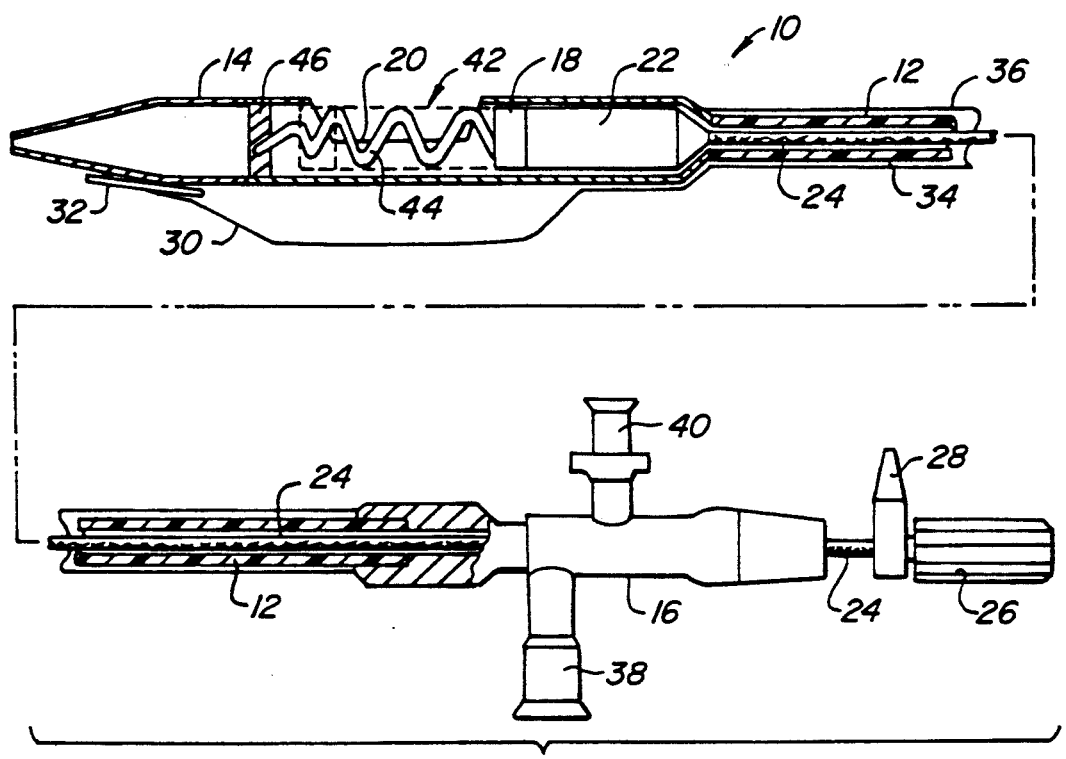
FIG. 1 illustrates a first catheter constructed in accordance with the principles of the present invention, where a circular cutting blade travels over a non-rotating elongate guide frame.

Referring now to FIG. 1, an atherectomy catheter 10 constructed in accordance with the principles of the present invention comprises a catheter body 12, a cylindrical housing 14 attached to the distal end of the catheter body 12, and a connector manifold 16 attached to the proximal end of the catheter body. A circular cutting blade 18 is disposed within the interior of cylindrical housing 14 and is mounted to be advanced past an elongate cutting aperture 20 formed in one side of said housing.

As illustrated, circular cutting blade 18 is secured to the forward end of a cylindrical shank 22, which in turn is secured at its proximal end to a torque cable 24, typically a braided cable or the like. Methods for constructing suitable braided structures are described in U.S. Pat. Nos. 4,425,919; 3,924,632; and 3,485,234, the disclosures of which are incorporated herein by reference. Torque cable 24 passes through manifold housing 16 and is secured at its distal end to a drive spindle 26. Drive spindle 26 is adapted to be connected to a motor drive unit of the type described in U.S. Pat. No. 4,771,774, the disclosure of which is incorporated herein by reference. A manual advance lever 28 is further provided in order to allow the user to axially advance and retract the cutting blade 18.

As illustrated, the drive mechanism is intended to advance the blade 18 in a forward or distal direction. It would, of course, be possible to reverse the direction of blade 18 and modify the drive mechanism so that the blade is advanced in the rearward or proximal direction to effect cutting.

Although the atherectomy catheter 10 will usually be adapted to rotate the cutting blade 18 as it is advanced, such rotation is not always required. Effective cutting can also be achieved by rotationally vibrating the blade 18 or, in some cases, by simply advancing the blade 18 without rotation or vibration.

An inflatable balloon 30 is formed on the outside of cylindrical housing 14 and disposed generally opposite to the location of the elongate aperture 20. Balloon 30 includes a distal vent tube 32 of the type generally described in U.S. Pat. No. 4,638,805 and pending application Ser. No. 07/234,397, the disclosures of which are incorporated herein by reference. The balloon may be inflated through an annular lumen 34 defined by an outer sheath 36 formed over catheter body 12. The fabrication of such coaxial inflation lumens is described in U.S. Pat. No. 4,411,055, the disclosure of which is incorporated herein by reference. An inflation port 38 is provided on the proximal housing 16 and is fluidly connected with the annular lumen 34 to allow for inflation of the balloon. A second port 40 is provided to allow for perfusion of fluids through central lumen 42 of the catheter body 12. Catheter body 12 will generally be a flexible tube having at least one lumen of the type generally employed in vascular catheters. Suitable materials and methods for forming such flexible catheter body tubes are described in U.S. Pat. No. 4,669,469, previously incorporated herein by reference.

As described thus far, the construction of atherectomy catheter 10 is generally conventional. The present invention lies in the provision of an elongate guide frame 42 within the interior of cylindrical housing 14. The elongate guide frame 42 defines an exterior guide surface which receives circular cutting blade 18 defines a path of travel which prevents loss of the blade from the housing. Additionally, the elongate guide frame 42 defines an interior volume which is capable of receiving and collecting the atheroma severed by blade 18 as it is advanced past the cutting aperture 20. Thus, the guide frame 18 will comprise an open framework which is capable of allowing the penetration of atheroma through adjacent frame members. In this way, blade 18 passing over the exterior of the guide frame 42 will sever the atheroma and allow the severed atheroma pieces to collect within the guide frame.

Elongate guide frame 42 may have a wide variety of geometries, with the only requirements being that it define the desired path of travel for the cutting blade 18 and that it allow penetration of the atheroma as just described. Usually, the guide frame 42 will have a substantially cylindrical surface to receive the cutting blade 18, although other geometries could be adapted. Conveniently, the elongate guide frame 42 may be a helical coil 44 which is attached at its distal end to an attachment block 46. The helical coil 44 defines a cylindrical guide surface on its exterior which is ideal for receiving and guiding the circular cutting blade 18. In addition, the atheroma is able to penetrate between successive turns of the coil, allowing the desired severing and collection of the atheroma pieces. Usually, the helical coil will have from about 1 to 10 turns per centimeter, more usually having from about 2 to 5 turns per centimeter. The coil may be formed from wire, ribbon, reinforced polymers, or the like.

Figure 1A:
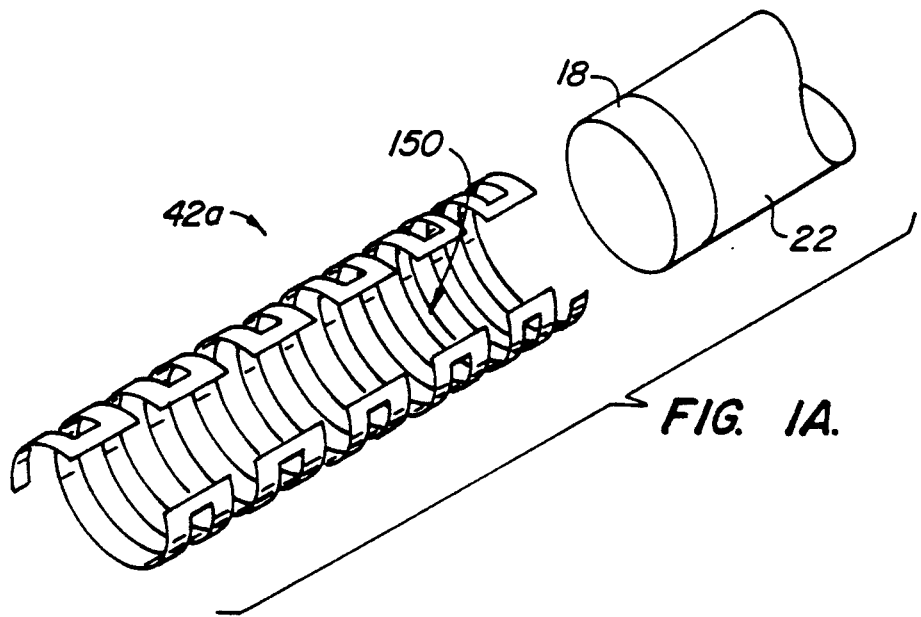
Figure 1B:
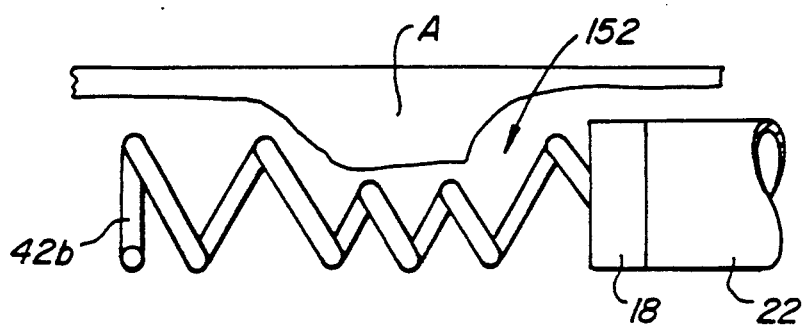

A first alternate construction of a guide frame 42a is illustrated in FIG. 1A. Guide frame 42a comprises a plurality of connected U-shaped segments which form an integral spring-like structure. Of particular advantage to the present invention, an axial gap 150 is left of one side of the frame 42a. By aligning the axial gap 150 with the elongate aperture 20 in housing 14, the penetration of atheroma into the guide frame 42a is facilitated. A second alternate construction of a guide frame 42b is illustrated in FIG. 1B. Guide frame 42b is formed generally as a helical coil, except that diameter of the helical winding is varied to provide one or more indentations 152 in the cylindrical surface thereof. Such indentations 152 are useful in allowing atheroma A to extend into the guide frame 42b to facilitate severing.

Preferably, the cylindrical housing 14 will be a flexible housing of the type described in U.S. Pat. No. 4,781,186, the disclosure of which has previously been incorporated herein by reference. Flexible housings may also be provided by other designs, including laminate constructions including a plurality of overlapping slotted housing where the slots are formed in an offset pattern, i.e., the slots in one layer are covered by the material of another layer. The slotted layers can be formed from machined metals, such as stainless steel, which may be thinned by chemical etching. Other suitable materials include thermosetting and thermoplastics, e.g., urethanes, polyvinyl chlorides, nylons, etc.

Helical coil 44 is particularly compatible with catheters 10 formed from flexible housings 14. The coil is inherently flexible and will conform to any bending or flexing of the housing 14 a it is advanced through bends and turns within the vascular system. Thus, the helical coil 44 will define a true path for the cutting blade 18 even when the housing 14 is bent into an arc or other configuration.

Figure 2:
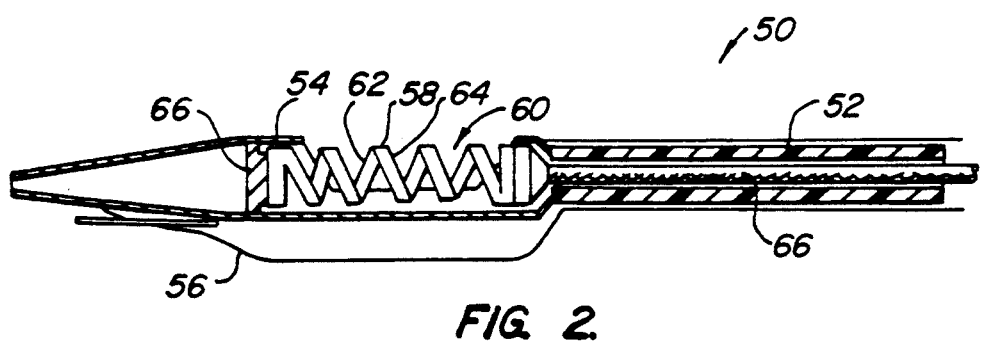
FIG. 2 illustrates a second catheter constructed in accordance with the principles of the present invention, where a rotating helical cutting blade is provided within a distal housing.

Referring now to FIG. 2, an atherectomy catheter 50 constructed in accordance with the principles of the present invention comprises a catheter body 52, a cylindrical housing 54, and an inflatable balloon 56, each of which is similar to the corresponding component described in connection with FIG. 1. Catheter 50, however, includes a helical cutting blade 58 which is mounted within the cylindrical housing 54 and is capable of rotating adjacent an elongate cutting aperture 60 formed within the housing. The helical cutting blade 58 includes at least one sharpened edge 62 and, usually, a second sharpened edge 64. In this way, cutting action can be obtained by rotating the blade 58 in either a clockwise or counterclockwise direction. It will be appreciated that a cutting action is obtained as the helical blade 58 is rotated because the successive turns of the helix effectively advance past the cutout 60. Even though the coil 58 remains in place within the housing 50, the individual turns of the blade appear to advance in much the same way that the stripes on a barber shop pole appear to advance as the cylinder is rotated. For this reason, the helical cutting blade is particularly advantageous since it remains in place and does not actually have to be moved relative to the housing. This greatly reduces the risk that the cutting blade 58 will be lost from the housing. Additionally, the cutting blade 58 is inherently flexible so that it will be able to conform to flexible housings as they are bent during use.

The helical cutting blade 58 may conveniently be rotated by a flexible torque cable 66 which is attached to the proximal end of the cutting blade 58. The distal end of the cutting blade 58, in turn, is attached to a bearing member 66 which allows free rotation of the helical cutting blade thereon.

Figure 2A:
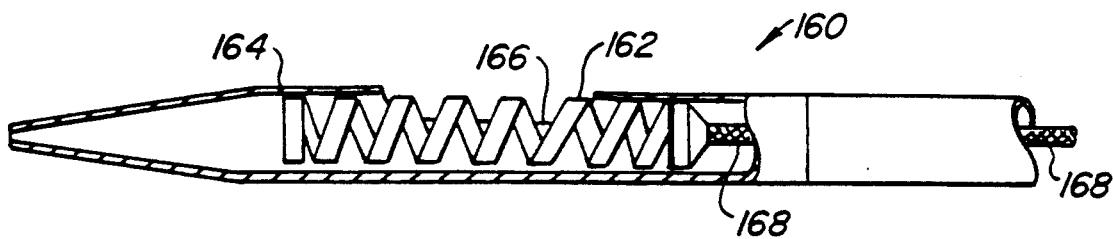

Referring now to FIG. 2A, an atherectomy catheter 160 having an axially-translatable helical cutting blade 162 is illustrated. Cutting blade 162 is mounted in housing 164 having an elongate aperture 166 and is attached to torque cable 168. The cutting blade 162 may thus be rotated and axially-translated by the torque cable 168. Usually, the blade 162 is sharpened on both edges so that severing may be effected as the blade is moved forward or backward within the housing 164.

Figure 2B:
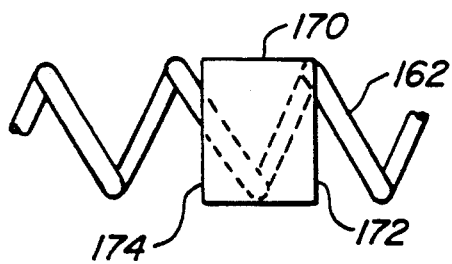
Figure 2C:
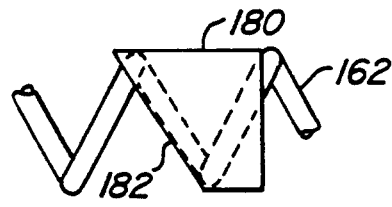
Figure 2D:
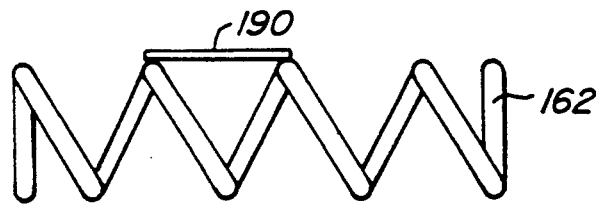

Referring now to FIGS. 2B–2C, additional blade elements may be secured to the helical blade 162, previously described. Blade element 170 (FIG. 2B) is a circular element which is sharpened along either or both edges 172 and 174. In this way, cutting is enhanced as the helical blade 162 is axially translated. Blade element 180 (FIG. 2D) is similar to element 170, except that an oblique cutting edge 182 is provided. Blade element 190 (FIG. 2D) is transversely mounted between adjacent turns of the helical blade 162 and cuts as the blade is rotated rather than as the blade is axially translated.

Figure 2E:
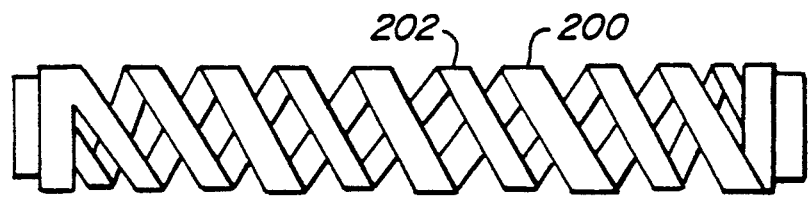

The embodiment of FIG. 2 may be further modified to provide for counter-rotating helical cutting blades 200 and 202, as illustrated in FIG. 2E. The blades 200 and 202 will normally have the opposite pitch, with blade 202 being mounted concentrically within blade 200. By rotating the blades 200 and 202 in the opposite directions, highly effective severing of atheroma can be achieved.

Figure 3:
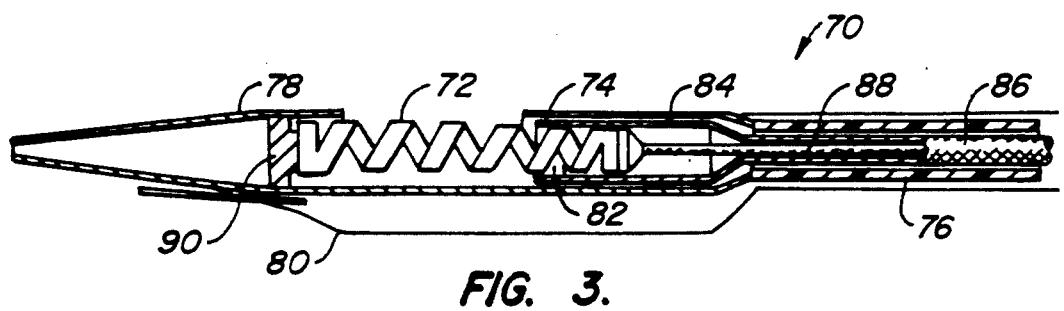
FIG. 3 illustrates a third catheter constructed in accordance with the principles of the present invention, where a circular cutting blade is adapted to travel over a rotating helical guide frame.

Referring now to FIG. 3, an atherectomy catheter 70 which combines both a helical cutting blade 72 and a circular cutting blade 74 will be described. The catheter 70 includes a catheter body 76, a cylindrical housing 78, and an inflation balloon 80, each of which is similar to the corresponding components described in connection with FIG. 1. Additionally, the catheter 70 includes a circular cutting blade 82 which, in turn, is attached to a hollow torque cable 86. The circular cutting blade 82 can thus be rotated and advanced using the torque cable 86, by means of the cable 86.

The helical cutting blade 72 is attached at its proximal end to a second flexible torque cable 88 and at its distal end to a bearing member 90. Thus, the helical cutting blade 72 can be rotated independently of the cutting blade 82. Enhanced severing and collection of the atheroma may be achieved by the use of both cutting actions.

It will be appreciated, however, that a helical guide member 44 (FIG. 1) may be substituted for the helical cutting blade 72. While such a construction will not provide for enhanced cutting, it will allow for the severed atheroma to be advanced within the helical structure by rotation of the helix.

Figure 4:
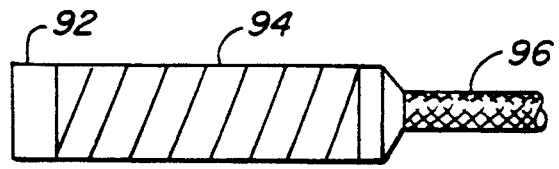
FIG. 4 illustrates a circular cutting blade having a flexible shank attached to a braided drive cable.

Referring now to FIG. 4, a preferred construction for the cutting blade assembly of FIGS. 1 and 3 is illustrated. Circular cutting blade 92 is secured to a flexible shank portion 94, which in turn is secured at its proximal end to a flexible torque cable 96. Preferably, the flexible shank is formed as a coiled ribbon where successive turns of the coil overlap, as illustrated.

Figure 5:
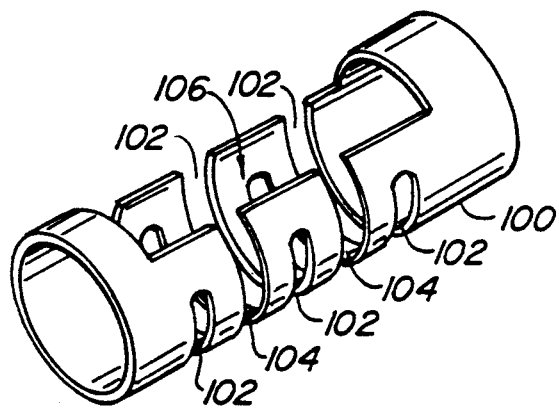
Figure 5A:
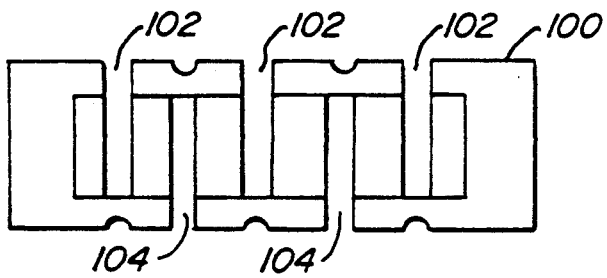

Referring now to FIGS. 5 and 5A, a particular construction for a flexible housing which may be utilized in any of the embodiments of FIGS. 1–3 is illustrated. Flexible housing 100 is typically formed from a rigid material, such as stainless steel. Housing 100, however, is machined to form a series of slots 102 and 104 which penetrate the cylindrical wall of the housing from opposite sides of the elongate aperture 106. The slots form independent segments in the housing and provide the desired flexibility without loss of circumferential stiffness. Optionally, the segmented housing 100 may be coated in a plastic material to enclose the interior without a substantial loss of flexibility.

Figure 6:
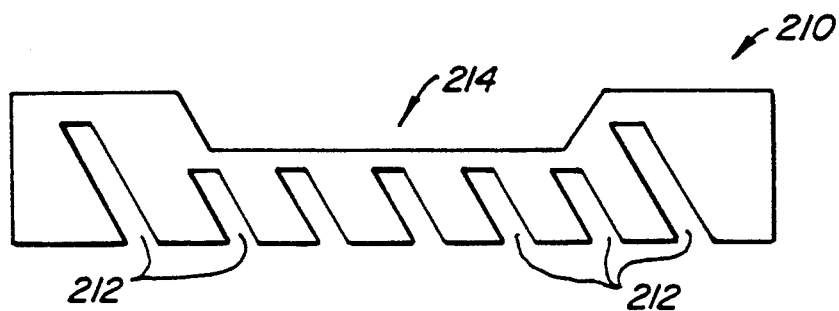
FIGS. 5 and 6 illustrate a particular construction for a flexible cylindrical housing which may be used in any of the catheters of FIGS. 1-3.

Referring now to FIG. 6, an alternate construction of a flexible housing 210 is illustrated. The housing may be formed from metal, rigid plastic, or formed on the side opposite from elongate aperture 214. The slots allow the housing 210 to flex in a single plane (aligned with the slots) about the axis. The degree of curvature obtainable, however, is limited by the number and the width of the slots 212. Once the adjacent edges of each slot 212 are in contact, the housing 210 will have reached the limit of its flexibility.

Flexible housing may also be formed as laminates of relatively thin, flexible layers which accommodate bending as the successive layers slide over one another.

Figure 7:
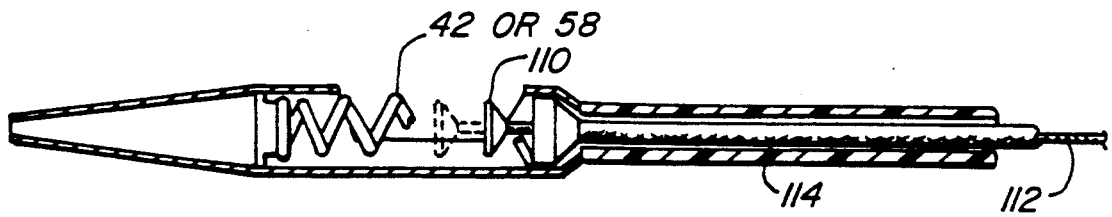
FIG. 7 illustrates a tamping mechanism which may be utilized with any of the catheters of FIGS. 1-3.

Referring now to FIG. 7, a tamping mechanism which may be utilized in connection with any of the embodiments of FIGS. 1–3 is illustrated. A tamping element 110 is secured to the distal end of a flexible cable 112. Usually, the flexible cable 112 will be located within the hollow interior of a flexible torque cable 114, which may be attached to either the helical cutting blade (as in FIG. 2) or a circular cutting blade (as in FIG. 1). Tamping element 110 is disposed to travel internally within either the elongate guide means of FIG. 1 or the helical members of FIGS. 2 or 3. The tamping member can then be used to push severed atheromic material forward within the guide member or helical blade to extend the period which the catheter may be used before it is necessary to remove an empty cylindrical housing.

For all of the embodiments discussed above, it will be possible to coat or fill the housings and/or cutting blades with a radiopaque material of filler in order to facilitate viewing under a fluoroscope. Suitable radiopaque coating materials include palladium and gold, with bismuth, barium, and tantalum being suitable as fillers. Alternately, they may be constructed of radiopaque materials such as tungstenrhenium or nitinol.

Although the foregoing invention has been described in detail for purposes of clarity of understanding, it will be obvious that certain modifications may be practiced within the scope of the appended claims.

What is claimed is:

1. An atherectomy catheter comprising:
    a catheter body having a lumen extending between proximal and distal ends thereof;
    a cylindrical housing secured to the distal end of the catheter body, said housing having a substantially open interior and an axially-aligned, elongate aperture on one side thereof;
    a first helical cutting blade disposed within the housing adjacent the elongate aperture;
    means for rotating the first helical cutting blade;
    a circular cutting blade disposed within the housing; and
    means for rotating and advancing the circular cutting blade over the helical cutting blade, whereby the helical cutting blade acts as a guide for the circular cutting blade.

2. An atherectomy catheter as in claim 1, wherein the cylindrical housing is flexible.

3. An atherectomy catheter as in claim 2, wherein the flexible cylindrical housing is segmented.

4. An atherectomy catheter as in claim 1, further comprising:
    a tamping surface disposed within the housing; and
    means for axially translating the tamping surface, whereby material severed by the helical cutting blade may be moved to one end of the cylindrical housing.

5. An atherectomy catheter as in claim 1, further comprising:
    a circular cutting blade disposed within the cylindrical housing, said circular cutting blade having an interior diameter sufficient to circumscribe the helical cutting blade; and
    means for rotating and axially advancing the cutting blade over the helical cutting blade.

6. An atherectomy catheter as in claim 5, wherein the circular cutting blade includes a cylindrical shank which receives the helical cutting blade as the circular cutting blade is rotated and advanced.

7. An atherectomy catheter as in claim 6, wherein the cylindrical shank of the cutting blade is flexible.

8. An atherectomy catheter as in claim 7, wherein the flexible shank comprises a coiled ribbon.

9. A method for severing atheroma within a blood vessel, said method comprising:
    positioning a housing within the blood vessel proximate the atheroma; and
    advancing a circular cutting blade over an elongate guide frame within the housing, said cutting blade being exposed to the atheroma through an opening in a side of the housing, whereby the atheroma is severed.

10. A method as in claim 9, further comprising rotating the circular cutting blade as it is advanced.

11. A method as in claim 9, wherein the elongate guide frame is a helical coil.

12. A method as in claim 11, further comprising rotating the helical coil as the cutting blade is advanced, whereby the severed atheroma is translated to one end of the housing.

13. A method as in claim 11, wherein at least one edge of the helical coil is sharpened to enhance severing of the atheroma.

14. A method as in claim 9, further comprising urging the opening of the housing against the atheroma to envelope at least a portion of the atheroma within the housing.

15. A method as in claim 14, wherein the housing is urged by inflating a balloon which is disposed on the housing on a side opposite to that of the opening.

* * * * *